United States Patent [19]

Murakami et al.

[11] 4,327,211
[45] Apr. 27, 1982

[54] METHOD FOR PREPARATION OF CEPHALOSPORIN COMPOUNDS

[75] Inventors: Masahiro Murakami; Masateru Kobayashi; Takanori Sone, all of Nobeoka; Chisei Shibuya, Fuji, all of Japan

[73] Assignee: Asahi Kasei Kogyo Kabushiki Kaisha, Japan

[21] Appl. No.: 210,746

[22] Filed: Nov. 26, 1980

[51] Int. Cl.³ .......................................... C07D 501/56
[52] U.S. Cl. ........................................ 544/27; 544/26
[58] Field of Search ........................................ 544/27

[56] References Cited

U.S. PATENT DOCUMENTS 4,258,195  3/1981  Shibuya et al. ...................... 544/27

Primary Examiner—Paul M. Couglan, Jr.

[57] ABSTRACT

A method for preparing a cephalosporin compound represented by the general formula (III)

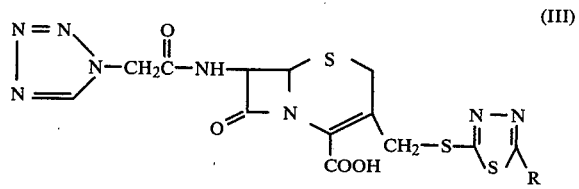

(wherein R represents hydrogen or methyl group) or a pharmaceutically acceptable salt thereof, which is characterized by reacting 7-amino-3-(benzimidazol-2-yl)-thiomethyl-3-cephem-4-carboxylic acid represented by the general formula (I)

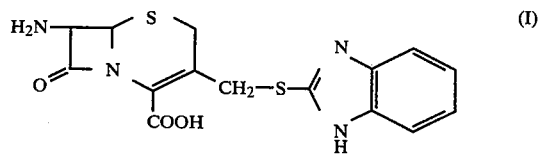

or a salt thereof with a compound represented by general formula (II)

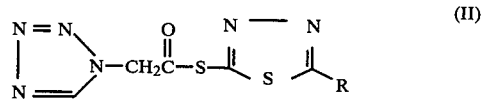

wherein R represents hydrogen or methyl group.

4 Claims, No Drawings

METHOD FOR PREPARATION OF CEPHALOSPORIN COMPOUNDS

FIELD OF THE INVENTION

This invention relates to a method for the preparation of cephalosporin compounds. More particularly, it relates to a method for the safe and efficient preparation of a compound represented by the general formula (III)

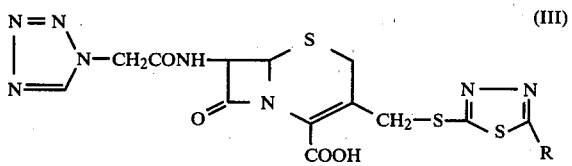

(wherein R represents hydrogen or a methyl group) or a pharmaceutically acceptable salt thereof which has an acid resistance and a strong bactericidal activity against a wide range of microorganisms (including Gram-positive and Gram-negative pathogens) and has already been marketed as an excellent antibiotic.

DESCRIPTION OF THE PRIOR ART

Heretofore, the compounds represented by the general formula (III) have been prepared in two steps from 7-aminocephalosporanic acid as the starting material. Among the methods for obtaining the compound (III), there is, for example, a method in which at first 7-(1H-tetrazol-1-ylacetamido)cephalosporanic acid is obtained from 7-aminocephalosporanic acid and 1H-tetrazole-1-acetic acid (Japanese Patent Publication No. 5,150/71) and then it is reacted with a 1,3,4-thiadiazole-5-thiol (Japanese Patent Publication No. 14,736/71) to obtain the intended compound of the general formula (III) and there is a method in which 7-amino-3-(1,3,4-thiadiazol-5-yl)thiomethyl-3-cephem-4-carboxylic acid is synthesized by the reaction of 7-aminocephalosporanic acid with a 1,3,4-thiadiazole-5-thiol (Japanese Patent Publication No. 17,936/64) and then it is reacted with 1H-tetrazole-1-acetic acid to obtain the compound of the general formula (III) (Japanese Patent Publication No. 35,751/71).

These methods each comprise a combination of two entirely independent reactions, the one being the acylation of the amino group at the position-3 of 7-aminocephalosporanic acid and the other the replacement of the acetoxy group in the acetoxymethyl group at the position-3 with a thiazolethio group. These two reactions proceed under different conditions and even if the two reactions are carried out consecutively, it is impossible to avoid an interruption of the reaction which is associated with the alteration of reaction conditions. Further, the cephalosporin compound becomes exposed to the conditions severe for its stability, i.e. a pH of 6.5 and a temperature of 60° C., for 3 to 6 hours in the former step of the above-noted two-step reaction and for 4 to 8 hours in the latter step. Thus, the decrease in yield of reaction product has posed a major problem from the economical viewpoint. It is also plausible that in purifying the intended product formed by consecutive reactions, the influence of unreacted starting materials and the impurities such as the compounds formed by decomposition is not negligible and, as a consequence, leaves a problem on the purity of the final product. As for the work conditions and safety, conventional methods have a serious defect in the moisture instability and the human skin irritating effect of the acylating agents which are commonly used in acylating the position-7 by the method of acyl chloride, mixed acid anhydride or DCC condensation.

In the replacement of acetoxy group at the position-3, on the other hand, although alkaline conditions are favorable for the enhancement of elimination reaction, yet the rapid skeletal decomposition of cephalo-type compounds under such conditions compels the reaction to be carried out under nearly neutral conditions where the reactivity is at a low level and the reaction requires a long time at 60° C. for its completion, meaning a serious drawback from the economical viewpoint. Because of the aforementioned defects, conventional methods are entirely unsatisfactory on an industrial scale.

SUMMARY OF THE INVENTION

The present inventors conducted extensive investigations on a process which overcomes the defects of conventional methods and permits the safe and efficient preparation of a compound of the general formula (III) or a pharmaceutically acceptable salt thereof and, as a result, found that a benzimidazolethio group bound to the methyl group at the position-3 of 7-amino-3-(benzimidazol-2-yl)thiomethyl-3-cephem-4-carboxylic acid

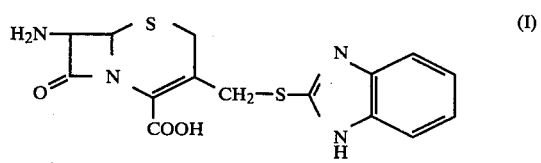

or a salt thereof is a leaving group having a high reactivity under the acidic conditions favorable for the stability of the cephalo-skeleton; and that a compound represented by the general formula (II)

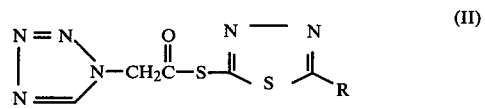

(wherein R represents hydrogen or methyl group) is a highly reactive group capable of efficiently introducing both the two substituent groups of the intended compound represented by the general formula (III) under identical conditions without interrupting the progress of reaction. It was further found that by using a combination of above-noted two compounds as starting material it is possible to achieve the object of said investigations, leading to the accomplishment of this invention.

Thus, the present invention provides a method for the preparation of a cephalosporin compound represented by the general formula (III)

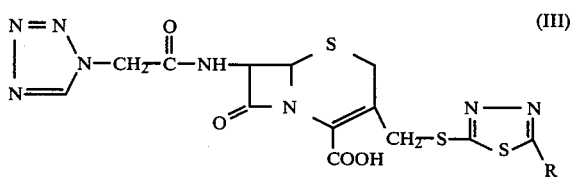

(wherein R is as defined above) or a salt thereof, which comprises reacting 7-amino-3-(benzimidazol-2-yl)-thiomethyl-3-cephem-4-carboxylic acid or a salt thereof with a compound represented by the general formula (II)

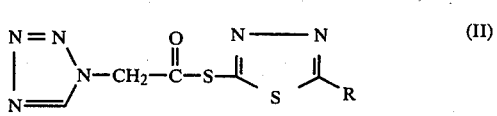

(wherein R is as defined above)

DESCRIPTION OF THE PREFERRED EMBODIMENT

The compound (I) used as a starting material in this invention is characterized in that the benzimidazolethio group bound to the methyl group at the position-3 is a leaving group which shows a high reactivity in the presence of proton. Proton is believed to catalyze the elimination reaction and the proton of the thiols present in the reaction system can be utilized to advantage so that in this case there is no need to add anew an acid catalyst. Analogous substituent groups to be bound to the methyl group at the position-3 include a benzthiazolethio group and a benzoxazolethio group. Although, in fact, the reaction proceeds with these substituent groups, a most distinguished effect is exhibited particularly by the benzimidazolethio group. Since this substituent group undergoes the replacement reaction very rapidly in the acidic region where the cephalo compounds are stable, its efficacy in terms of material yield is twice or more as much as that of the acetoxy group used in conventional methods.

The compound (I) can be obtained by the method already known by itself. It is obtained, for example, by the known reaction between the commercial 7-aminocephalosporanic acid and the 2-mercaptobenzimidazole already used as an antioxidant for polymers and is sold on the market at a low price. It is also obtained by reacting 7-(glutaramido)cephalosporanic acid with 2-mercaptobenzimidazole and then cleaving the amide linkage in the side chain attached at the position-7 by the action of 7β-(4-carboxybutanamido)-cephalosporanic acid acylase disclosed in Japanese Patent Application Laid-open No. 101,584/75.

The compound represented by the general formula (II) which is used as the other starting material is not a mere acylating agent. It is a single compound having both reactive groups, the one being capable of acylating at the position-7 of cephalosporanic acid and the other being capable of substituting at the position-3. It is highly active and has a great advantage of efficiently advancing the reaction, resulting in a high yield of the intended compound (III).

More particularly, the reactivity of the compound (II) is comparable to that of an acyl chloride or a mixed acid anhydride which has been said to be of highest activity. It has been known as one of the disadvantages of conventional acylating methods that unless the reaction temperature is strictly controlled, side reactions tend to occur, thereby decreasing the efficiency, whereas in the case of the compound (II) side reactions including polymerization and decomposition will not take place at a temperature in a usually practicable temperature range of, for example, from room temperature up to 80° C. One of the other known acylating techniques is the method of active thioesters such as, for example, phenyl thioester of a carboxylic acid. This method is not applicable to the cephalo compounds because of severe reaction conditions involving the presence of a strong alkali, a high temperature and a long reaction time extending to several hours, while if this method is used under mild conditions, the acylation will not proceed (see Comparative Example 1). It is indeed an unexpected and surprising fact that although being a type of thioesters, the compound (II) is a reagent of high reactivity under mild conditions.

The compound (II) is yellow columnar crystals which are nonhygroscopic, non-irritating and noncorrosive, contributing greatly to the ease in handling, to the safety of working environment and workers, and to the maintainance of equipment. Therefore, in practice it is really an excellent starting material without parallel.

Further, it is to be noted about the compound (II) that although being a single compound, it is able to participate simultaneously in two reactions, is highly active and when combined with the high susceptibility of the compound (I) to elimination reaction, it can increase the efficiency of the reaction and reduce the reaction time, contributing greatly also to the economy of the present preparative process.

The advantage of the present invention in transforming the compound (III) at the positions 7 and 3 may be expressed in terms of numerical value in the following way: in conventional methods, the overall yield of the isolated compound (III) is 10.4% when the procedures of Japanese Patent Publication Nos. 5,150/71 and 14,736/71 are combined and 34.5% when the procedures of Japanese Patent Publication Nos. 17,936/64 and 35,751/71 are combined, whereas the yield jumps up to 95% according to this invention.

The compound (II) may be prepared in a high yield by reacting a 1,3,4-thiadiazole-5-thiol represented by the general formula (IV)

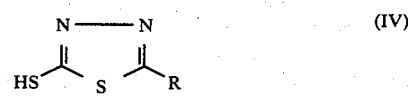

(wherein R represents hydrogen or methyl group) or a derivative thereof with 1H-tetrazole-1-acetic acid or a derivative thereof in a solvent at −50° to 100° C. (Japanese Patent Application Laid-open No. 20,711/80).

The intended compound represented by the general formula (III) or a pharmaceutically acceptable salt thereof can be easily and efficiently derived from the reaction in a solvent between the compound represented by the general formula (I) obtained above or a salt thereof and the compound represented by the general formula (II).

The amount of compound (II) should be equimolar or more to the amount of compound (I), preferably 1.0 to 2.0 moles from the economical viewpoint. Preferred solvents are amides such as N,N-dimethylformamide, N,N-diethylformamide, N,N-dimethylacetamide, and N,N-diethylacetamide or those containing water. Other solvents are, for example, ethers such as Methyl Cellosolve, aliphatic ketones such as acetone and methyl ethyl ketone, halogenated hydrocarbons such as dichloromethane and chloroform, nitriles such as acetonitrile and propionitrile, and sulfoxides such as dimethyl sulfoxide and diethyl sulfoxide. The reaction can proceed by using these solvents each alone or in mixtures or in mixtures with water. Of these solvents, amides such as N,N-dimethylformamide and N,N-dimethylacetamide or mixtures of amides with water are especially preferred in view of solubility, conversion and economy.

Since one of the features of the present method is the presence of thiol compounds in the reaction system, which are formed from the compound (II) and by the replacement reaction, the additional acid catalyst is not necessary. However, it is preferable for the reduction in reaction time and the improvement in the yield of reaction product to add acid catalysts including mineral acids such as hydrochloric acid and sulfuric acid and organic acid including sulfonic acids such as p-toluenesulfonic acid and methanesulfonic acid, fatty acids such as propionic acid, and thiols such as 2-mercaptothiadiazole. With respect to yield and reduction in reaction time, mineral acids and thiols are preferred.

A sufficient amount of additional acid catalyst is substantially 0.05 mole or more per mole of compound (I).

The reaction temperature depends upon the presence or absence of the catalyst and the type of solvent. Although a suitable temperature range is from 10° to 100° C., the particularly preferred temperature range is from 30° to 80° C. in view of the conversion and the stability of cephalosporin skeleton.

Although depending upon the presence or absence of the catalyst and the type of solvent, a sufficient reaction time is generally in the range of from 30 minutes to 10 hours. For instance, a reaction time of 30 minutes to 4 hours is sufficient for the reaction conducted in the presence of an acid catalyst in aqueous N,N-dimethylformaldehyde at 60° C., whereas a reaction time of 8 to 18 hours is necessary in the conventional methods when the acylation at the position-7 and the replacement reaction at the position-3 are conducted consecutively. The method of this invention is very simple and economically superior when the side reactions between the reactants and the decomposition of the reaction products are taken into account.

The intended compound in this invention may be isolated in crystalline form by extraction of the reaction mixture in a customary manner or if an anhydrous solvent was used, by converting into sodium or potassium salt in a customary manner.

If necessary, the cephalosporin compound represented by the general formula (III) obtained according to this invention can be converted into a pharmaceutically acceptable salt. The conversion into an alkali metal salt, ammonium salt, or an alkaline earth metal salt can be effected in a customary manner. These salts show excellent properties, such as, for example, solubility in water, which are useful in formulating a drug preparation.

According to this invention, it is possible to prepare safely and in a high yield cephalosporin compounds represented by the general formula (III) and pharmaceutically acceptable salts thereof which are excellent antibiotics having high antimicrobial activities.

The invention is illustrated below in further detail with reference to Examples, but the invention is not limited thereto.

EXAMPLE 1

Into a 3-liter three-necked flask provided with a thermometer, were charged 36 g of 7-amino-3-(benzimidazol-2-yl)thiomethyl-3-cephem-4-carboxylic acid, 29 g of 2-methyl-1,3,4-thiadiazol-5-ylthiol ester of 1H-tetrazoleacetic acid, 1.1 liters of N,N-dimethylformamide, and 0.9 liter of water. After heating the mixture to 60° C., 100 ml of 0.5 N aqueous hydrochloric acid was further added to serve as catalyst for the reaction. The mixture was stirred at 60° C. for 2 hours to complete the reaction. On analysis of the reaction solution by high speed liquid chromatography the conversion was found to be 95%. After cooling, the reaction solution was freed from impurities by extraction with diethyl ether in a customary manner, then pH was decreased to 1.5 with 1 N aqueous hydrochloric acid, extracted three times with 2 liters of ethyl acetate, dried over anhydrous magnesium sulfate, and concentrated under reduced pressure to obtain 40.7 g of 7-(1H-tetrazol-1-ylacetamido)-3-(2-methyl-1,3,4-thiadiazol-5-ylthiomethyl)-3-cephem-4-carboxylic acid in the form of white powder (97% purity).

$\lambda_{max} = 272$ nm (3% aqueous sodium bicarbonate solution); melting point: 197°–200° C. (decomp.)

NMR spectrum (DMSO-$d_6$), $\delta_{ppm}$: 2.68 (S, 3H), 3.71 (dd, 2H), 4.39 (dd, 2H), 5.12 (d, 1H), 5.37 (S, 2H), 5.73 (q, 1H), 9.33 (S, 1H), 9.49 (d, 2H).

COMPARATIVE EXAMPLE 1

Into a 50-ml three-necked flask provided with a thermometer, were charged 272 mg of 7-aminocephalosporanic acid, 11 ml of N,N-dimethylformamide, and 9 ml of water to form a solution. After adding 220 mg of phenyl thioester of 1H-tetrazoleacetic acid, the solution was heated to 30° C. On analysis of the reaction solution after 2 hours by high speed liquid chromatography, no reaction product but the starting materials were found.

EXAMPLE 2

Into a 500-ml three-necked flask provided with a thermometer, were charged 1.5 g of 7-amino-3-(benzimidazol-2-yl)thiomethyl-3-cephem-4-carboxylic acid, 2.8 g of 1,3,4-thiadiazol-5-ylthiol ester of 1H-tetrazoleacetic acid, 110 ml of N,N-dimethylformamide, and 90 ml of water and the mixture was heated to 60° C. After 15 minutes, 10 ml of 0.5 N aqueous hydrochloric acid was added and the mixture was stirred at 60° C. for 30 minutes to complete the reaction. On analysis of the reaction mixture by high speed liquid chromatography the conversion was found to be 88%. After cooling, the reaction solution was freed from the impurities with diethyl ether, then pH was decreased to 1.5 with 1 N aqueous hydrochloric acid and extracted three times with 200 ml of ethyl acetate. After drying over anhydrous magnesium sulfate, the solution was concentrated under reduced pressure to obtain 3.7 g of 7-(1H-tetrazol-1-ylacetamido)-3-(1,3,4-thiadiazol-5-ylthiomethyl)-3-cephem-4-carboxylic acid as a white powder (95% purity).

$\lambda_{max} = 273$ nm (3% aqueous sodium bicarbonate solution).

EXAMPLE 3

Into a 100-ml three-necked flask provided with a thermometer, were charged 720 mg of 7-amino-3-(benzimidazol-2-yl)thiomethyl-3-cephem-4-carboxylic acid, 560 mg of 1,3,4-thiadiazol-5-ylthiol ester of 1H-tetrazoleacetic acid, 22 ml of N,N-dimethylacetamide, and 18 ml of water and the mixture was heated to 90° C. The mixture was stirred at 90° C. for 30 minutes to complete the reaction. On analysis of the reaction solution by high speed liquid chromatography, the conversion was found to be 93%. After cooling, the reaction solution was freed from the impurities with diethyl ether in a customary manner, then pH was decreased to 1.5 with 1 N aqueous hydrochloric acid, and extracted three times with 40 ml of ethyl acetate. After drying over anhydrous magnesium sulfate, the solution was concentrated to obtain 775.3 mg of 7-(1H-tetrazol-1-ylacetamido)-3-(1,3,4-thiadiazol-5-ylthiomethyl)-3-cephem-4-carboxylic acid as a white powder (95% purity).

EXAMPLE 4

Into a 50-ml three-necked flask provided with a thermometer, were charged 362 g of 7-amino-3-(benzimidazol-2-yl)thiomethyl-3-cephem-4-carboxylic acid, 290 mg of 2-methyl-1,3,4-thiadiazol-5-ylthiol ester of 1H-tetrazoleacetic acid, and 20 ml of N,N-dimethylformamide to form a solution and the solution was heated to 30° C. Anhydrous hydrogen chloride was introduced into the solution. The hydrogen chloride stream was turned off when 10 millimoles had been introduced, as determined from the flow rate, and the solution was stirred as such for 6 hours. On analysis of the reaction solution by high speed liquid chromatography the conversion was found to be 68%. After cooling, the reaction solution was freed from the N,N-dimethylformamide under reduced pressure, then dissolved again in an aqueous sodium bicarbonate solution, and subjected to separation and purification with a synthetic adsorbent column to obtain 254.3 mg of 7-(1H-tetrazol-1-ylacetamido)-3-(2-methyl-1,3,4-thiadiazol-5-ylthiomethyl)-3-cephem-4-carboxylic acid as a white powder (97% purity).

EXAMPLE 5

Into a 5-liter three-necked flask provided with a thermometer, were charged 362 mg of 7-amino-3-(benzimidazol-2-yl)thiomethyl-3-cephem-4-carboxylic acid, 900 ml of acetone, and 1 liter of water to form a solution. After adding a solution of 290 mg of 2-methyl-1,3,4-thiadiazol-5-ylthio ester of 1H-tetrazoleacetic acid in 100 ml of acetone, the solution was heated to 60° C., further admixed with 2 ml of 0.5 N aqueous hydrochloric acid, and the reaction was allowed to proceed for 4 hours. On analysis of the reaction solution by high speed liquid chromatography, the conversion was found to be 66%. After cooling, pH was decreased with 1 N hydrochloric acid, and the reaction solution was subjected to separation and purification with a synthetic adsorbent column in a customary way to obtain 273.6 mg of 7-(1H-tetrazol-1-ylacetamido)-3-(2-methyl-1,3,4-thiadiazol-5-ylthiomethyl)-3-cephem-4-carboxylic acid as a white powder (93% purity).

EXAMPLE 6

The reaction was allowed to proceed in the same manner as in Example 5, except that Methyl Cellosolve was used in place of the acetone. The conversion was 59% and the product was 258 mg of a white powder (88% purity).

EXAMPLE 7

The reaction was allowed to proceed in the same manner as in Example 1, except that the following solvents were used in place of the N,N-dimethylformamide. The results were as shown in the following table.

| Solvent employed | Conversion | Yield in weight | Purity |
|---|---|---|---|
| Acetonitrile | 73% | 32.3 g | 87% |
| Dimethyl sulfoxide | 83% | 35.9 g | 89% |

EXAMPLE 8

The reaction was allowed to proceed in the same manner as in Example 4, except that the following catalysts were used in place of the anhydrous hydrogen chloride. The results were as shown in the following table.

| Catalyst species | Weight of catalyst | Conversion | Yield in weight | Purity |
|---|---|---|---|---|
| Anhydrous tin tetrachloride | 260 mg | 51% | 255 mg | 77% |
| Anhydrous aluminum chloride | 133 mg | 52% | 267 mg | 75% |

EXAMPLE 9

The reaction was allowed to proceed in the same manner as in Example 1, except that sulfuric acid was used in place of the hydrochloric acid. The conversion was 95% and the product was 40.8 g of a white powder (95% purity).

EXAMPLE 10

Into a 50-ml three-necked flask provided with a thermometer, were charged 362 mg of 7-amino-3-(benzimidazol-2-yl)thiomethyl-3-cephem-4-carboxylic acid, 290 mg of 2-methyl-1,3,4-thiadiazol-5-ylthiol ester of 1H-tetrazoleacetic acid, 15 ml of N,N-dimethylformamide, and 5 ml of water and the mixture was heated to 60° C. Thereafter, 95 mg of p-toluenesulfonic acid was added and stirring was continued for 4 hours to complete the reaction. On analysis of the reaction solution by high speed liquid chromatography the conversion was found to be 89%. After cooling, the reaction solution was freed from impurities with diethyl ether in a customary manner, then pH was decreased to 1.5 with 1 N aqueous hydrochloric acid, extracted three times with 40 ml of ethyl acetate, dried over anhydrous magnesium sulfate, and concentrated under reduced pressure to obtain 412.8 mg of 7-(1H-tetrazol-1-ylacetamido)-3-(2-methyl-1,3,4-thiadiazol-5-ylthiomethyl)-3-cephem-4-carboxylic acid as a white or pale yellow powder (88% purity).

EXAMPLE 11

Into 20 ml of water, were dissolved 9.2 g of the product obtained in Example 1 and 1.7 g of sodium bicarbonate. The solution was filtered, the filtrate was admixed with 90 ml of 99% ethanol, and the crystals were collected by filtration to obtain sodium 7-(1H-tetrazol-1-ylacetamido)-3-(2-methyl-1,3,4-thiadiazol-5-ylthiomethyl)-3-cephem-4-carboxylate in crystalline form.

$\lambda_{max}$: 272 nm (3% aqueous sodium bicarbonate solution).

NMR (DMSO-$d_6$) $\delta_{ppm}$: 2.70 (s, 3H), 3.67 (dd, 2H), 4.57 (dd, 2H), 5.08 (d, 1H), 5.47 (s, 2H), 5.65 (q, 1H), 9.50 (s, 1H), 9.72 (d, 2H).

What is claimed is:

1. A method for preparing a cephalosporin compound represented by the formula (III)

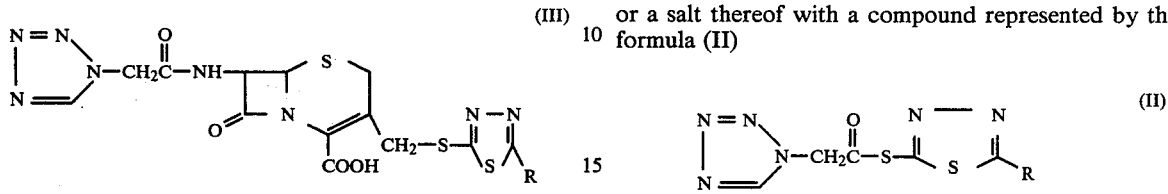

wherein R represents hydrogen or methyl group, or a pharmaceutically acceptable salt thereof, which comprises reacting 7-amino-3-(benzimidazol-2-yl)thiomethyl-3-cephem-4-carboxylic acid represented by the formula (I)

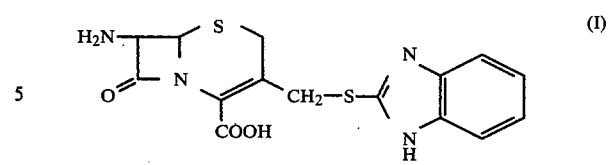

or a salt thereof with a compound represented by the formula (II)

wherein R represents hydrogen or methyl group, in the presence of an acidic catalyst.

2. A method according to claim 1, wherein the acidic catalyst is hydrochloric acid or sulfuric acid.

3. A method according to claim 1, wherein a solvent which is an aprotic polar solvent or an aprotic polar solvent containing water is used.

4. A method according to claim 3, wherein the aprotic polar solvent is N,N-dimethylformamide or N,N-dimethylacetamide.

* * * * *